US00PP15645P2

(12) United States Plant Patent
Olesen et al.

(10) Patent No.: US PP15,645 P2
(45) Date of Patent: Mar. 8, 2005

(54) ROSE PLANT NAMED 'POULAC009'

(50) Latin Name: *Rosa hybrida*
Varietal Denomination: POULac009

(75) Inventors: L. Pernille Olesen, Fredensborg (DK); Mogens N. Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 0 days.

(21) Appl. No.: 10/738,878

(22) Filed: Dec. 16, 2003

(51) Int. Cl.[7] ..... A01H 5/00
(52) U.S. Cl. ..... Plt./151
(58) Field of Search ..... Plt./151

*Primary Examiner*—Anne Marie Grunberg
*Assistant Examiner*—Annette H Para

(57) ABSTRACT

A new garden rose plant of the compact floribunda class which has abundant, dark red flowers and attractive foliage. This new and distinct variety has shown to be uniform and stable in the resulting generations from asexual propagation.

2 Drawing Sheets

Botanical classification: *Rosa hybrida.*
Variety denomination: 'POULac009'.

SUMMARY OF THE INVENTION

The present invention constitutes a new and distinct variety of garden rose plant which originated from a controlled crossing between the female parent, 'POULgrad', described and illustrated in U.S. Plant Pat. No. 11,610 dated Oct. 31, 2000, and the male parent, an unnamed seedling. The two parents were crossed during the summer of 1997 and the resulting seeds were planted in a controlled environment in Fredensborg, Denmark. The new variety is named 'POULac009'.

The new variety may be distinguished from its female seed parent, 'POULgrad', by the following combination of characteristics:

1. While the seed parent, 'POULgrad', has an average flower diameter of 55 mm. 'POULac009' is 65 mm to 75 mm.
2. While the seed parent, 'POULgrad', has general tonality Red Group 53A. 'POULac009' is Red-Purple Group 60A.

The new variety may be distinguished from its male pollen parent by the following combination of characteristics:

1. While the pollen parent is light pink in color, 'POULac009' is dark red.
2. While the pollen parent is a floribunda rose, with a normal growth habit, 'POULac009' is compact.

The objective of the hybridization of this rose variety was to create a new and distinct variety for garden use with unique qualities, such as:

1. Uniform and abundant dark red flowers which do not fade;
2. Vigorous, but compact growth when propagated both as a budded rose and on its own roots;
3. Disease resistance;
4. Good branching characteristics.

This combination of qualities is not present in previously available commercial cultivars of this type, known to the inventors, and distinguish 'POULac009' from all other varieties of which we are aware.

As part of their rose development program, L. Pernille Olesen and Mogens N. Olesen germinated the seeds from the aforementioned hybridization during winter of 1997 and conducted evaluations on the resulting seedlings in a controlled environment in Fredensborg, Denmark.

'POULac009' was selected in the spring 1998 by the inventors as a single plant from the progeny of the aforementioned hybridization.

Asexual reproduction of 'POULac009' by traditional budding and rooted cuttings was first done by L. Pernille and Mogens N. Olesen in their nursery in Fredensborg, Denmark in July, 1998. This initial and other subsequent asexual propagations conducted in controlled environments have demonstrated that the characteristics of 'POULac009' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems, of 'POULac009'.

Specifically illustrated in SHEET 1:

FIG. 1.1; Open flower, stem showing open flower, branching, and the attachment of leaves, buds, and peduncles;

FIG. 1.2; Flower bud and partially opened flower;

FIG. 1.3; Flower petals, detached;

Specifically illustrated in SHEET 2:

FIG. 2.1; Sepals, receptacle, peduncle;

FIG. 2.2; Bare stem exhibiting thorns;

FIG. 2.3; Mature leaves. Upper surface exhibiting leaf glossiness and lower surface exhibiting anthocyanin.

DETAILED DESCRIPTION OF THE VARIETY

The following is a description of 'POULac009', as observed in its growth in a field nursery in Jackson County, Oreg. Observed plants are 3 years of age grown on *Rosa multiflora* understock. Color references are made using The Royal Horticultural Society (London, England) Colour Chart, 1995, except where common terms of color are used.

For a comparison, several physical characteristics of the rose variety 'POULchris', a rose variety from the same inventors described and illustrated in U.S. Plant Pat. No. 11,151 and issued on Dec. 14, 1989, are compared to 'POULac009' in Chart 1.

CHART 1

| | 'POULac009' | 'POULchris' |
|---|---|---|
| Average diameter of flower bloom when open | 40 mm to 50 mm when. | 60 mm. |
| Color after opening, petals, upper surface. | Red-Purple Group 60B to 60C. | Red Group 53A. |
| Leaf size. | 37 mm to 55 mm (l) × 29 mm to 34 mm (w). | 70 mm (l) × 100 mm (w). |

Parents:

*Female seed parent.*—'POULgrad'.

*Male pollen parent.*—Unnamed seedling.

FLOWER AND FLOWER BUD

Blooming habit: Continuous.

Flower bud:

*Size.*—Upon opening, 20 mm in length from base of receptacle to end of bud.

*Bud form.*—Short and globular.

*Bud color.*—As sepals unfold, petals are Red-Purple Group 59A. At ¼ opening petals are Red-Purple Group 59A.

*Sepals.*—Upper Surface: Color: Yellow-Green Group 144A. Texture: Smooth. Moderately pubescent. Lower Surface: Color: Yellow Green Group 143B. Anthocyanic pigments the color of Greyed-Purple Group 183B observed in the center and on the foliaceous appendages. Texture: Smooth. Sparse stipitate glands. Sepal Shape: Sepal apex is cirrhose. Base is flat at union with receptacle. Sepal Margin: Margins have medium foliaceous appendages on three of the five sepals. Size: 20 to 25 mm (l) by 6 mm (w).

*Receptacle.*—Surface Texture: Smooth and glabrous. Shape: Urn-shaped. Size: 8 mm (h)×7 mm (w). Color: Yellow-Green Group 144A. Anthocyanin: Greyed-Purple Group 183B.

*Peduncle.*—Surface: Smooth and glabrous. Length: 32 to 35 mm. Color: Yellow-Green Group 144A with intonations of Greyed-Purple Group 184B.

*Borne.*—12 flower buds per stem on average.

Flower bloom:

*Fragrance.*—Light floral scent.

*Duration.*—The blooms have a duration on the plant of approximately 7 to 10 days. Petals fall cleanly away from plant.

*Size.*—Flower diameter is 40 to 50 mm when open.

*Form.*—Open cup.

*Shape of flower when viewed from the side.*—Upon opening, upper part: Cupped. Upon opening, lower part: Concave. Open flower, upper part: Flattened convex. Open flower, lower part: Concave.

Petalage: 65 to 75 petals under normal conditions with 10 to 15 petaloids.

Color:

Upon opening, petals:

*Outermost petals.*—Outer side: Red-Purple Group 60B to 60C. Inner Side: Red Group 53A.

*Innermost petals.*—Outer side: Red-Purple Group 60B to 60C. Inner Side: Red Group 53A.

Upon opening, basal petal spots:

*Outermost petals.*—Outer side: Yellow Group 9A. Inner Side: Yellow Group 9A.

*Innermost petals.*—Outer side: Yellow Group 9A. Inner Side: Yellow Group 9A.

After opening, petals:

*Outermost petals.*—Red-Purple Group 60B to 60C. Inner Side: Red Group 53A.

*Innermost petals.*—Outer size: Red-Purple Group 60B to 60C. Inner Side: Red Group 53A.

After opening, basal petal spots:

*Outermost petals.*—Outer side: Yellow Group 9A. Inner side: Yellow Group 9A.

*Inner most petals.*—Outer side: Yellow Group 9A. Inner side: Yellow Group 9A.

General tonality: On open flower Red-Purple Group 60A. No change in the general tonality at the end of the $10^{th}$ day. Afterwards, general tonality is Red-Purple Group 60A.

Petals:

*Petal reflex.*—Petals reflex slightly.

*Margin.*—Entire. Slight undulations and a point in center of margin observed.

*Shape.*—Apex: Round. Base: Acute.

*Size.*—20 to 25 mm (l)×20 to 23 mm (w).

*Texture.*—Smooth.

*Thickness.*—Thin.

*Arrangement.*—Not Formal.

Petaloids:

*Color.*—Upper Surface: Red-Purple Group 59A to 59B. Lower Surface: Red-Purple Group 59A to 59B.

*Size.*—10 mm (l)×7 mm (w).

Reproductive organs:

*Pistils.*— Length: 4 to 5 mm. Quantity: 32.

*Pollen.*—Color: Greyed-Orange Group 163B. Quantity: Scant.

*Anthers.*—Size: 2 mm long. Color: Greyed-Orange Group 163B with center Greyed-Red Group 180B. Quantity: 65 (actual count).

*Filaments.*—Color: Greyed-Orange Group 163A. Length: 4 mm.

*Stigmas.*—Even in location to the height of the filaments and anthers. Color: Greyed-Yellow Group 160B.

*Styles.*—Color: Yellow-Green Group 154D.

*Hips.*—None Observed in the field nursery in Jackson County Oreg.

PLANT

Plant growth: Moderate, upright to bushy. When grown as a budded field grown plant on *Rosa multiflora* understock, the height of the plant is 40 cm to 60 cm. Average width is 40 cm.

Stems:

*Color.*—Young wood: Yellow-Green Group 146A. Older wood: Yellow-Green Group 146B. Surface Texture: Young wood: Smooth. Older wood: Smooth.

Thorns:

*Incidence.*—23 thorns per 10 cm of stem.

*Size.*—Average length: 8 mm to 10 mm.

*Color.*—Yellow-Green Group 146B to 146C. With light intonations of Greyed-Purple 183D.

*Shape.*—Concave.

Plant foliage: Normal number of leaflets on normal leaves in middle of the stem: 5 leaflets.

*Compound leaf size.*—135 mm (l)×100 mm (w).

*Quantity.*—Average.

*Color.*—Mature Foliage: Upper Leaf Surface: Yellow-Green Group 147A to 147B. Lower Leaf Surface: Yellow-Green Group 147C to 147B. Juvenile foliage: Upper Leaf Surface: Yellow-Green Group 146A to 146B. Lower Leaf Surface: Yellow-Green Group 147A to 147B. Anthocyanin: Location: Margins of juvenile leaflets. Color: Greyed-Purple Group 183A.

Plant leaves and leaflets:

*Stipules.*—Size: 24 mm in length. Color: Yellow-Green Group 144A. Margins: Finely serrated with few stipitate glands.

*Petiole.*—Length: 35 mm to 45 mm. Color: Yellow-Green Group 144B. Anthocyanin: Greyed-Red Purple Group 184B observed. Underneath: Smooth with prickles.

*Rachis.*—Length: 35 mm to 45 mm. Color: Yellow-Green Group 144B. Anthocyanin: Greyed-Red Purple Group 184B observed. Underneath: Smooth with prickles.

*Leaflet.*—Size: 37 to 55 mm (l)×29 to 34 mm (w). Edge: Finely serrated. Shape: Ovate with cuspidate apex. Base shape is round. Texture: Smooth. Arrangement: Odd pinnate. Venation: Reticulate. Glossiness: Moderately glossy.

Disease resistance: Above average resistance to mildew, rust, black spot, and Botrytis under normal growing conditions in Jackson County, Oreg.

Cold hardiness: The variety 'POULac009' has been found to be cold tolerant to USDA Cold Hardiness Zone 6.

It is claimed:

1. A new and distinct variety of rose plant of the compact floribunda rose class, substantially as herein illustrated and described as a distinct and novel rose variety due to its abundant dark red, disease resistance, and extended period of bloom.

* * * * *

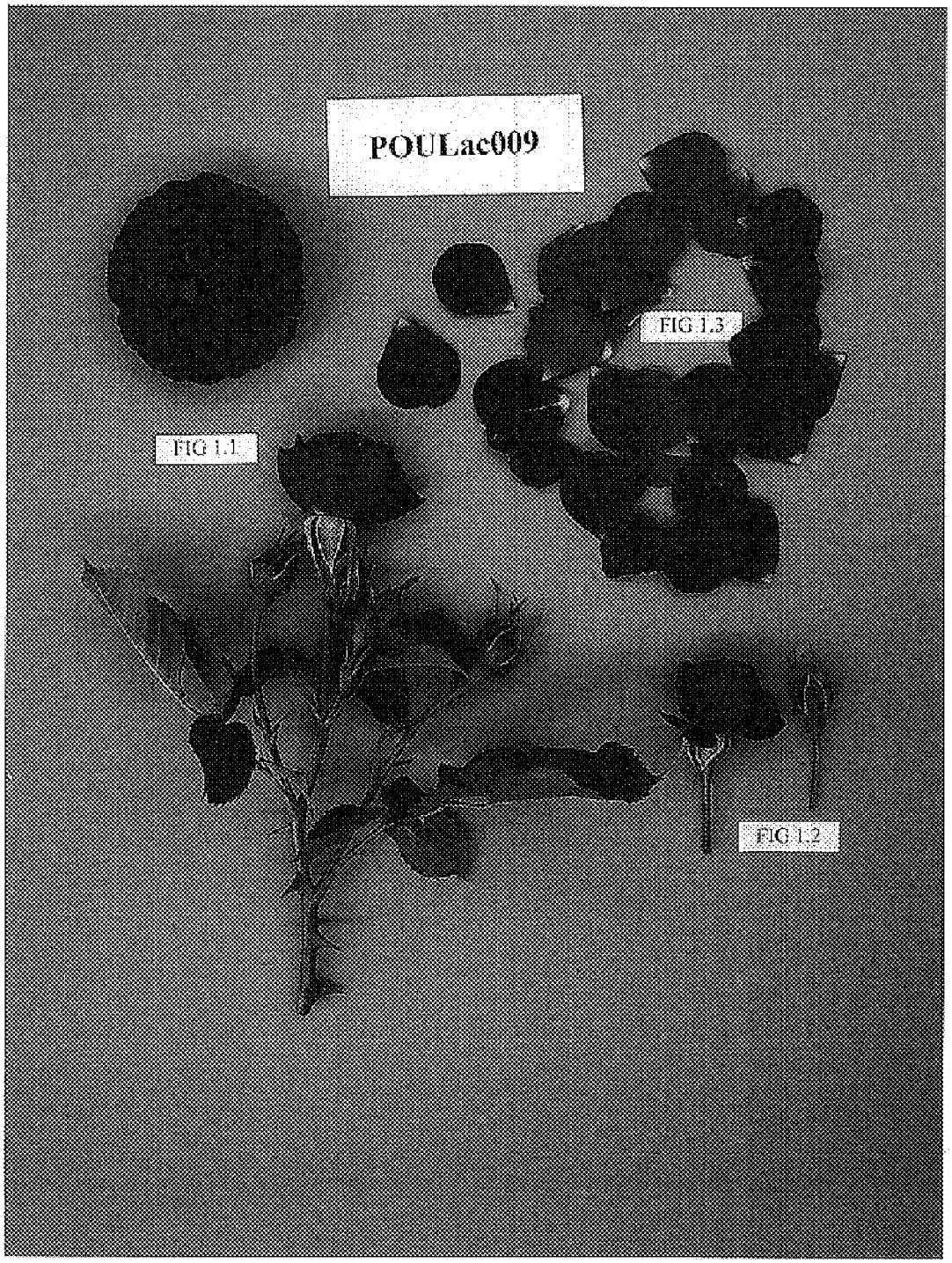
POULac009
FIG 1.1
FIG 1.2
FIG 1.3

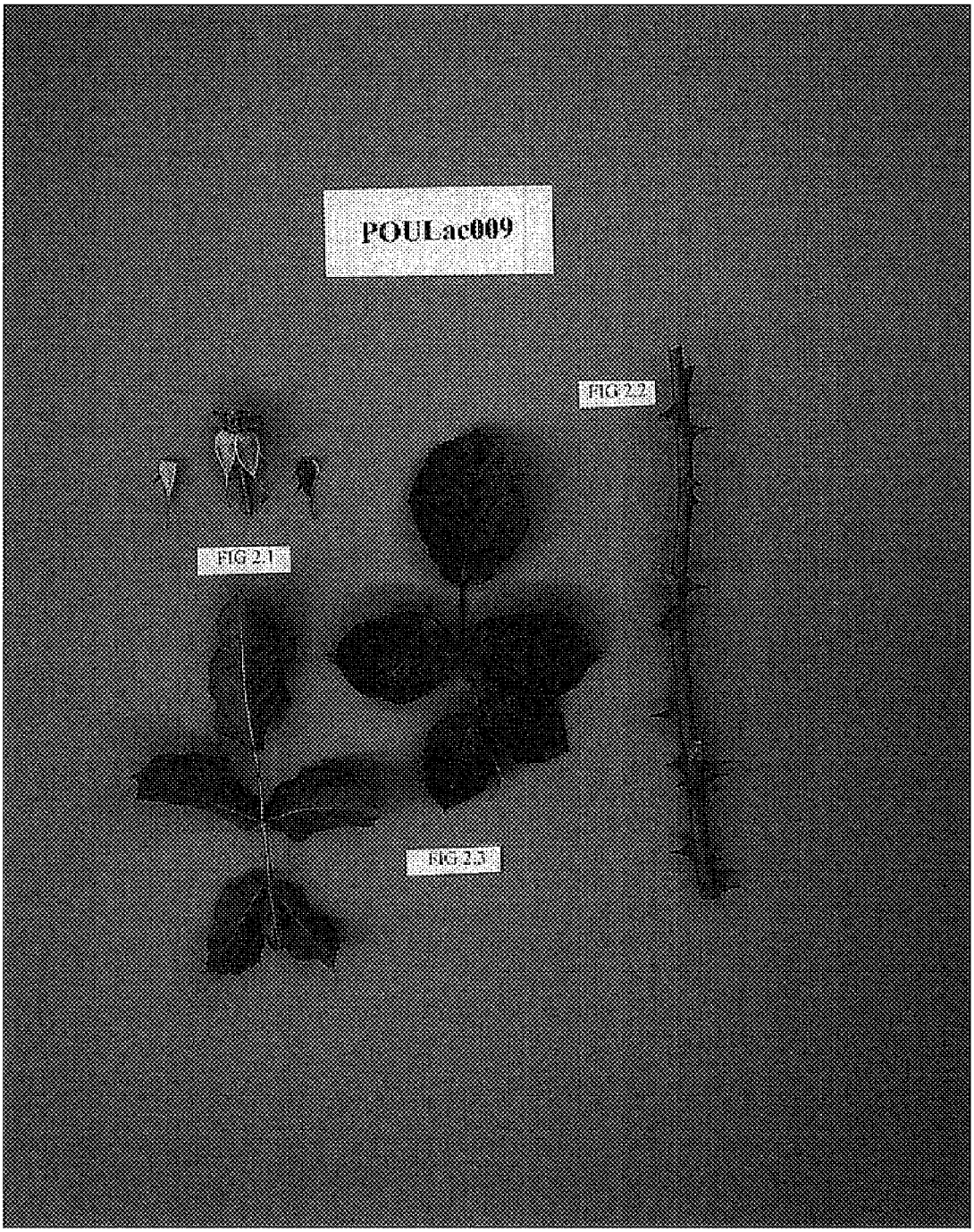
POULac009
FIG 2.1
FIG 2.2
FIG 2.3